United States Patent
Wang et al.

(10) Patent No.: US 10,428,073 B2
(45) Date of Patent: Oct. 1, 2019

(54) SALT TYPE AND CRYSTAL TYPE OF 4H-PYRAZOLO [1, 5-ALPHA] BENZIMIDAZOLE COMPOUND AND PREPARATION METHOD AND INTERMEDIATE THEREOF

(71) Applicants: HUBEI BIO-PHARMACEUTICAL INDUSTRIAL TECHNOLOGICAL INSTITUTE INC., Wuhan, Hubei (CN); HUMANWELL HEALTHCARE (GROUP) CO., LTD., Wuhan, Hubei (CN)

(72) Inventors: Xuehai Wang, Hubei (CN); Charles Z. Ding, Shanghai (CN); Jie Shen, Hubei (CN); Shuhui Chen, Shanghai (CN); Lie Li, Hubei (CN); Gang Li, Shanghai (CN); Yong Xu, Hubei (CN); Cailin Wang, Shanghai (CN); Ronghua Tu, Hubei (CN); Jimeng Wang, Shanghai (CN); Yang Yue, Hubei (CN); Biao Deng, Shanghai (CN); Hailiang Chen, Hubei (CN); Hui Liu, Shanghai (CN); Wenjie Sun, Hubei (CN); Cong Wang, Shanghai (CN); Lu Huang, Hubei (CN); Zheng Wang, Shanghai (CN); Weidong Li, Shanghai (CN)

(73) Assignees: Hubei Bio-Pharmaceutical Industrial Technological Institute Inc., Wuhan (CN); Humanwell Healthcare (Group) Co., Ltd., Wuhan (CN)

( * ) Notice: Subject to any disclaimer, the term of this patent is extended or adjusted under 35 U.S.C. 154(b) by 0 days.

(21) Appl. No.: 15/763,676

(22) PCT Filed: Sep. 29, 2016

(86) PCT No.: PCT/CN2016/100821
§ 371 (c)(1),
(2) Date: Mar. 27, 2018

(87) PCT Pub. No.: WO2017/054755
PCT Pub. Date: Apr. 6, 2017

(65) Prior Publication Data
US 2018/0258093 A1  Sep. 13, 2018

(30) Foreign Application Priority Data
Sep. 30, 2015 (CN) .......................... 2015 1 0643088

(51) Int. Cl.
*C07D 487/04* (2006.01)
*C07D 401/04* (2006.01)
*C07C 57/145* (2006.01)

(52) U.S. Cl.
CPC .......... *C07D 487/04* (2013.01); *C07C 57/145* (2013.01); *C07D 401/04* (2013.01); *C07B 2200/13* (2013.01)

(58) Field of Classification Search
CPC . C07B 2200/13; C07C 57/145; C07D 401/04; C07D 487/04
See application file for complete search history.

(56) References Cited

U.S. PATENT DOCUMENTS 6,696,437 B1   2/2004 Lubisch et al.

FOREIGN PATENT DOCUMENTS

| CN | 1353695 A | 6/2002 |
|---|---|---|
| CN | 101506214 A | 8/2009 |
| CN | 101981013 A | 2/2011 |
| CN | 104974161 A | 10/2015 |
| WO | WO-2007/149907 A2 | 12/2007 |
| WO | WO-2009118382 A1 | 10/2009 |
| WO | WO 2015/154630 | * 10/2015 |

OTHER PUBLICATIONS

Jan. 5, 2017 International Search Report issued in International Patent Application No. PCT/CN2016/100821.
Jan. 5, 2017 Written Opinion of the International Searching Authority issued in International Patent Application No. PCT/CN2016/100821.
Protective Groups in Organic Synthesis, Wiley and Sons, 1991.
Chinese application 201510643088.3 filed on Sep. 30, 2015 (without publication).

* cited by examiner

*Primary Examiner* — Valerie Rodriguez-Garcia
(74) *Attorney, Agent, or Firm* — Harness Dickey & Pierce, P.L.C.

(57) ABSTRACT

Disclosed in the present invention are a salt type and crystal type of 4H-pyrazolo[1,5-alpha]benzimidazole compound and a preparation method and intermediate thereof. The 4H-pyrazolo[1,5-alpha]benzimidazole compound is represented by formula I:

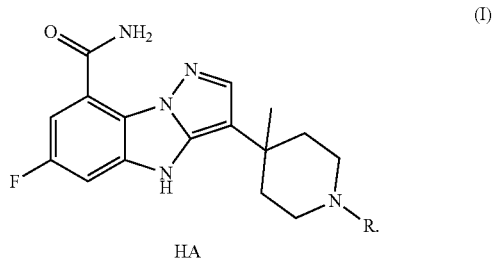

13 Claims, 3 Drawing Sheets

SALT TYPE AND CRYSTAL TYPE OF 4H-PYRAZOLO [1, 5-ALPHA] BENZIMIDAZOLE COMPOUND AND PREPARATION METHOD AND INTERMEDIATE THEREOF

CROSS REFERENCE TO RELATED APPLICATIONS

This application is a U.S. National Phase Application under 35 U.S.C. 371 of International Application No. PCT/CN2016/100821 filed on Sep. 29, 2016 and published in Chinese as WO 2017/054755A1 on Apr. 6, 2017. This application is based on and claims the benefit of priority from Chinese Patent Application No. 201510643088.3 filed Sep. 30, 2015. The entire disclosures of all of the above applications are incorporated herein by reference.

FIELD OF INVENTION

The present invention relates to a salt type and crystal type of 4H-pyrazolo[1,5-α]benzimidazole compound and preparation method and intermediate thereof.

PRIOR ARTS

Application No. or Patent No. 201410144173.0 describes a new class of PARP inhibitor that serves as an independent therapy for tumor types of DNA repair mechanisms of BRCA1 and BRCA2 deletion type. It also works as a sensitizer when a combination treatment with many types of anti-cancer therapies such as DNA alkylating agents, platinum drugs, topoisomerase inhibitors and radiation therapy is conducted, this greatly enhances the antitumor efficacy of first-line chemotherapy drugs. Its structure is shown in formula (B-1):

The anti-cancer drug Veliparib (ABT-888), developed by AbbVie, is a novel poly (ADP-ribose) polymerase (PARP) inhibitor and poly (ADP-ribose) polymerase (PARP) is a DNA repair enzyme that plays a key role in the DNA repair pathway. Veliparib, a novel highly selective PARP inhibitor, works by interfering with the DNA repair process in cells, making tumors more sensitive to DNA-damaging chemotherapy drugs.

CONTENT OF THE PRESENT INVENTION

The present invention provides a preparation method of the compound of formula (I), comprising the following steps:

wherein,
R is optionally selected from $C_{1-5}$ alkyl;
$R_1$ is an amino protecting group;
X is a halogen;
the metal catalyst is selected from a palladium metal catalyst, a platinum metal catalyst and/or a copper metal catalyst;
the ligand is selected from a phosphine-containing ligand coordinated to a palladium metal catalyst and/or a nitrogen-containing ligand coordinated to a copper metal catalyst;
the base is selected from an alkali metal base, an alkaline earth metal base, an organic base and/or an organometallic base.

In some embodiments of the present invention, R is selected from the group consisting of a methyl, an ethyl, an isopropyl or a tert-butyl.

In some embodiments of the present invention, $R_1$ is selected from an alkoxycarbonyl amino protecting group and/or a benzyl amino protecting group.

In some embodiments of the present invention, $R_1$ is selected from the group consisting of Bn, Cbz, Boc, Fmoc, Alloc, Teoc, methoxycarbonyl and ethoxycarbonyl.

In some embodiments of the present invention, the palladium metal catalyst is selected from the group consisting of $Pd_2(dba)_3$, $Pd(PPh_3)_4$, $Pd(dppf)Cl_2$, $Pd(PPh_3)_2Cl_2$, $Pd(OAc)_2$ and/or $PdCl_2$.

In some embodiments of the present invention, the platinum metal catalyst is selected from $PtO_2$.

In some embodiments of the present invention, the copper metal catalyst is selected from the group consisting of CuI, CuBr, CuCl, Cu and/or $Cu_2O$.

In some embodiments of the present invention, the phosphine-containing ligand coordinated to the palladium metal catalyst is selected from Xantphos, Sphos, Xphos, Ruphos and/or Brettphos.

In some embodiments of the present invention, the nitrogen-containing ligand coordinated to the copper metal catalyst is selected from 1,2-cyclohexanediamine, N,N'-dimethylethylenediamine and/or 1,10-phenanthroline.

In some embodiments of the present invention, the alkali metal base is selected from the group consisting of lithium hydroxide, sodium hydroxide, potassium hydroxide, cesium hydroxide, sodium carbonate, potassium carbonate, cesium carbonate, sodium bicarbonate, potassium bicarbonate and/or potassium phosphate.

In some embodiments of the present invention, the alkaline earth metal base is selected from sodium hydride, potassium hydride and/or calcium hydride.

In some embodiments of the present invention, the organic base is selected from triethylamine, DIPEA, NMM and/or DBU.

In some embodiments of the present invention, the organometallic base is selected from sodium methoxide, lithium tert-butoxide, sodium tert-butoxide, potassium tert-butoxide, sodium ethoxide and/or aluminum isopropoxide.

In some embodiments of the present invention, the molar ratio of the compound (II) to the base is 1:1-5, specifically 1:2-3.

In some embodiments of the present invention, the mole ratio of the compound (II) to the metal catalyst is 1:0.05-0.1.

In some embodiments of the present invention, the molar ratio of the metal catalyst to the ligand is 1:1-2.

In some embodiments of the present invention, the reaction is conducted at 100 to 150° C., specifically 120 to 140° C.

In some embodiments of the present invention, the reaction time is 5 to 12 hours, specifically 5 to 6 hours.

In some embodiments of the present invention, the reaction is performed in a reaction solvent, and the reaction solvent is selected from amide solvents.

In some embodiments of the present invention, the amide solvent is selected from DMF, DMAC, NMP and/or DMSO.

In some embodiments of the present invention, the amount of the reaction solvent is 5 to 20 times, more preferably 8 to 12 times, the weight of compound (II).

In some embodiments of the present invention, the preparation method of the compound of formula (I) also comprises the following reaction:

[Chemical reaction scheme showing compound (III) reacting with Carbon monoxide, ammonia source, Metal catalyst, ligand, base to form compound (IV)]

wherein,
the metal catalyst, ligand and base are as defined above;
the ammonia source is selected from HMDS and/or formamide;
the reaction solvent is selected from amide solvents, specifically from DMF, DMAC, NMP and/or DMSO;
the pressure of carbon monoxide is 0.1-2 MPa, specifically 0.8-1 MPa;
the mole ratio of the compound (III) to the base is 1:1-5, specifically from 1:2-3;
the mole ratio of the compound (III) to the metal catalyst is 1:0.05-0.1;
the mole ratio of the compound (III) to the ammonia source is 1:1.2-10, specifically 3-5;
the molar ratio of the metal catalyst and the ligand is 1:1-2;
the amount of the reaction solvent is 5 to 20 times, specifically 8 to 12 times, the weight of the compound (III);
the reaction is conducted at 80 to 110° C., specifically 100 to 110° C.;
the reaction time is 12 to 24 hours, specifically 18 to 20 hours.

In some embodiments of the present invention, the preparation method of the compound of formula (I) also comprises the following reaction:

[Chemical reaction scheme showing compound (IV) reacting with HB to form compound (V)]

wherein,
HB is selected from an organic or inorganic acid;
the molar ratio of the compound (IV) to the acid is 1:1-10, specifically 1:5-8;
the reaction solvent is selected from the group consisting of water, glacial acetic acid, alcohol solvents, ether solvents, ester solvents and/or any mixtures thereof;
the amount of the reaction solvent is 3 to 20 times, specifically 5 to 10 times the weight of the compound (IV);
the reaction is conducted at −10 to 30° C.;
the reaction time is 2 to 3 hours.

In some embodiments of the present invention, the above alcoholic solvent is selected from methanol, ethanol and/or isopropanol.

In some embodiments of the present invention, the ether solvent is selected from the group consisting of THF, 2-METHF and/or dioxane.

In some embodiments of the present invention, the ester solvent is selected from ethyl acetate.

In some embodiments of the present invention, the organic acid is selected from trifluoroacetic acid, methanesulfonic acid, p-toluenesulfonic acid, citric acid, maleic acid or fumaric acid.

In some embodiments of the present invention, the inorganic acid is selected from hydrochloric acid, hydrobromic acid, phosphoric acid and/or sulfuric acid.

In some embodiments of the present invention, the preparation method of the compound of formula (I) also comprises the following reaction:

wherein, the base is as described above;

the molar ratio of the compound (V) to the base is 1:1-5, specifically 1:1-2;

the reaction solvent is selected from water, alcoholic solvents and/or any mixture thereof;

the amount of the reaction solvent is 5 to 20 times, specifically 8 to 12 times, the weight of the compound (V);

the reaction is conducted at 0 to 10° C., specifically 0 to 5° C.

In some embodiments of the present invention, the preparation method of the compound of formula (I) also comprises the following reaction:

wherein, the hydrogen source is selected from hydrogen gas, cyclohexene and/or ammonium formate;

R aldehyde is selected from the group consisting of formaldehyde, acetaldehyde and isobutyraldehyde;

R ketone is selected from isopropanone;

the reaction solvent is selected from amide solvents;

the amount of the reaction solvent is 5 to 20 times, more preferably 8 to 12 times the weight of the compound (VI);

the mole ratio of the compound (VI) to the reagent R is 1:10, specifically 1:5-10;

the mole ratio of the compound (VI) to the metal catalyst is 1:0.05-0.1;

the pressure of hydrogen gas is 0.1 to 2 MPa, specifically 0.8 to 1 MPa;

the temperature is conducted at 60 to 100° C., specifically 60 to 70° C.

In some embodiments of the present invention, the amide solvent is selected from DMF, DMAC, NMP and/or DMSO, and more preferably NMP.

In some embodiments of the present invention, the preparation method of the compound of formula (I) also comprises the following reaction:

in some embodiments of the present invention, HA is selected from an organic or inorganic acid;

the reaction solvent is an alcoholic solvent and/or a mixed solvent containing an alcoholic solvent and water;

the volume ratio of the alcoholic solvent to water is 1:0.05-0.1;

the amount of the reaction solvent is 5 to 20 times, specifically 8 to 12 times, the weight of the compound (VII);

the mole ratio of the compound (VII) to the reagent HA is 1:0.5-2, specifically 1:1.05-1.2.

the reaction is conducted at 50 to 100° C., specifically 60 to 80° C.;

the organic acid, the inorganic acid and the alcoholic solvent are as defined above.

In some embodiments of the present invention, the preparation method of the compound of formula (I) also comprises the following reaction:

(II)

(III)

(IV)

HB
(V)

(VI)

(VII)

HA
(I)

The present invention also provides an intermediate for the preparation of compound (I), which has a structure selected from the group consisting of (II)

(III)

(IV)

-continued

(V)

and (VI)

The present invention further provides a preparation method of intermediate (II), comprising wherein, the mole ratio of the compound (f) to the compound (h) is 1:1-1.2.

the molar ratio of the compound (f) to the base is 1:1-5;

the reaction solvent is selected from methanol, ethanol, isopropanol, THF, 2-METHF, acetonitrile, NMP, DMF and/or DMAc;

the amount of the solvent is 5 to 20 times the weight of the compound (f);

the reaction is conducted at 50 to 100° C.;

the base is as defined above.

The present invention also provides a compound 2 having a structure of

Compound 2

Figure 1:
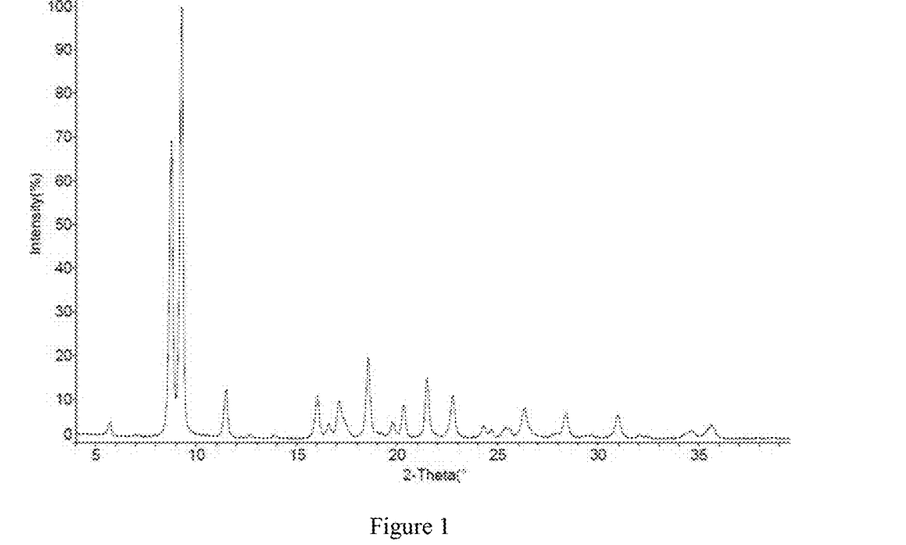
FIG. 1 is the XRPD pattern of Cu-Kα radiation of the crystal type A.

The present invention also provides crystal type A of compound 3, characterized by an XRPD pattern as shown in FIG. 1, Compound 3

In some embodiments of the present invention, the analysis data of the XRPD pattern of the crystal type A is as shown in Table 1:

TABLE 1 analysis data of XRPD pattern of crystal type A

| NO. | 2-Theta | d (A) | I % |
|---|---|---|---|
| 1 | 5.718 | 15.4432 | 3.2 |
| 2 | 8.773 | 10.0706 | 68.9 |
| 3 | 9.286 | 9.5154 | 100.0 |
| 4 | 11.512 | 7.6804 | 11.0 |
| 5 | 16.051 | 5.5172 | 10.0 |
| 6 | 16.622 | 5.3289 | 2.4 |
| 7 | 17.136 | 5.1704 | 8.3 |
| 8 | 18.575 | 4.7727 | 18.1 |
| 9 | 19.780 | 4.4848 | 3.2 |
| 10 | 20.332 | 4.3642 | 7.5 |
| 11 | 21.513 | 4.1272 | 13.6 |
| 12 | 22.776 | 3.9011 | 9.6 |
| 13 | 24.315 | 3.6575 | 2.7 |
| 14 | 24.672 | 3.6054 | 1.8 |
| 15 | 25.401 | 3.5036 | 2.1 |
| 16 | 26.327 | 3.3824 | 6.6 |
| 17 | 28.436 | 3.1362 | 5.7 |
| 18 | 31.001 | 2.8823 | 5.5 |
| 19 | 34.572 | 2.5923 | 1.3 |
| 20 | 35.618 | 2.5185 | 3.0 |

In some embodiments of the present invention, the differential scanning calorimetry curve of the crystal type A has starting points of endothermic peaks at 85.44° C., 162.95° C., 205.63° C. respectively.

Figure 2:
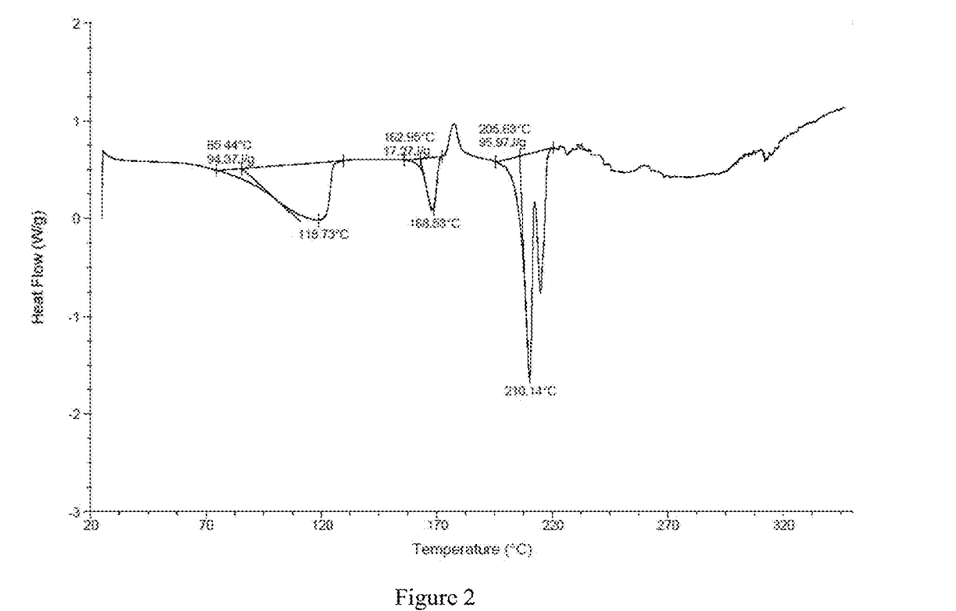
FIG. 2 is the DSC graph of the crystal type A.

In some embodiments of the present invention, DSC pattern of the crystal type A is as shown in FIG. 2.

In some embodiments of the present invention, the thermogravimetric profile of the crystal type A showing a weight loss of up to 3.740% at 129.34° C., up to 0.4250% at 194.30° C. and up to 13.59% at 245.46° C.

Figure 3:
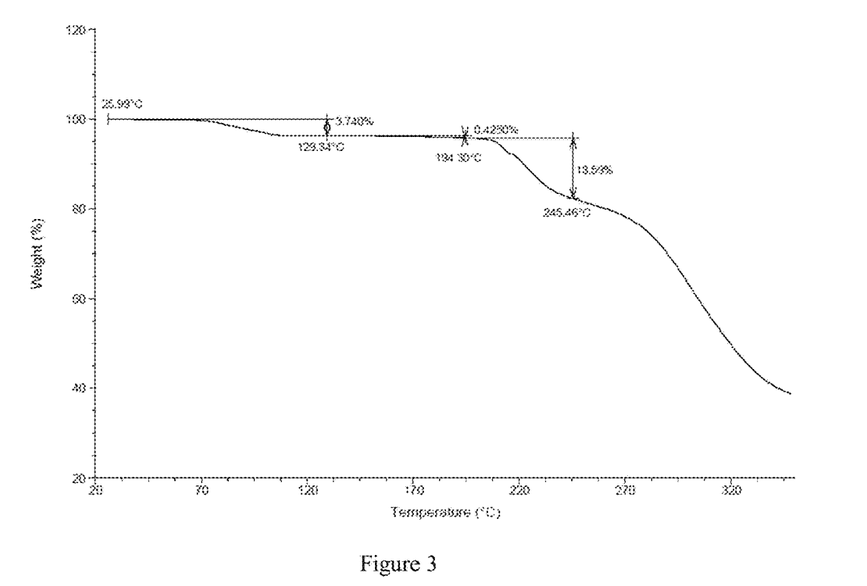
FIG. 3 is the TGA graph of the crystal type A.
Figure 4:
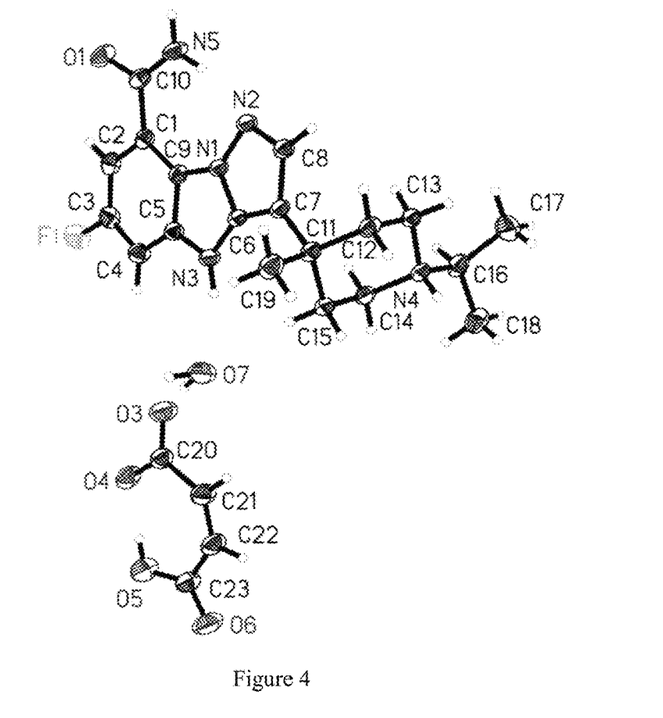
FIG. 4 is the three-dimensional structure ellipsoid diagram of the single molecule of compound 3.
Figure 5:
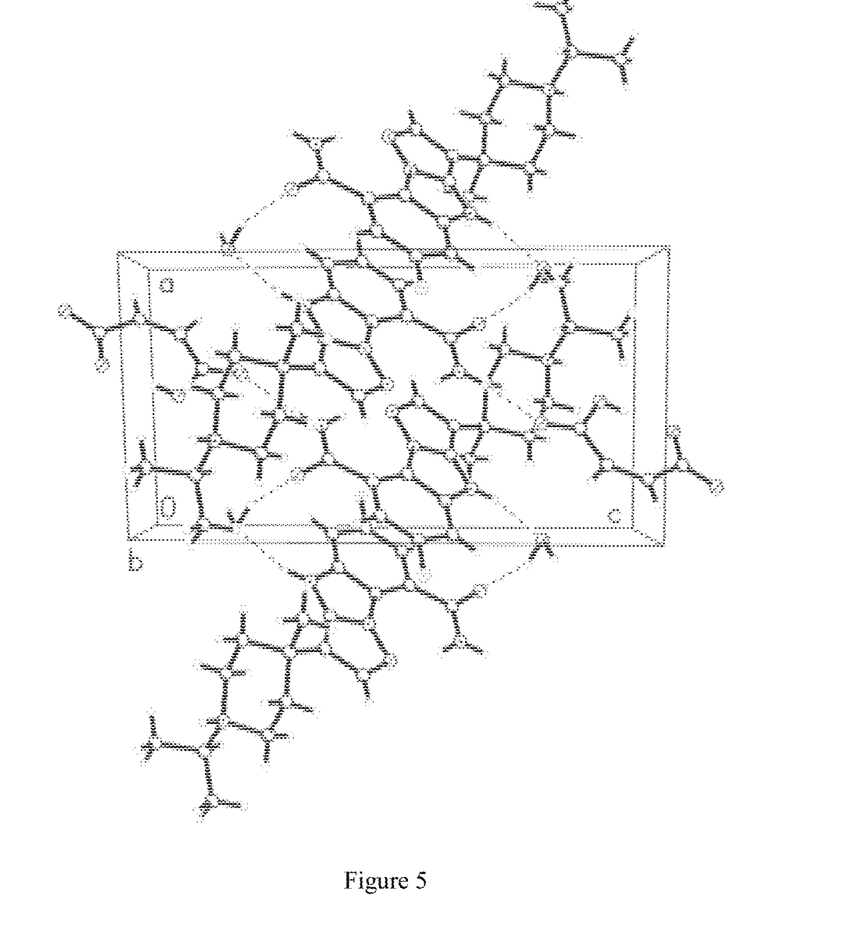
FIG. 5 is the crystal cell packing diagram of the crystal type A in b-axis direction.

In some embodiments of the present invention, the TGA pattern of the crystal type A is as shown in FIG. 3.

The present invention also provides a preparation method of the crystal type A, comprising adding the compound of formula (I) in any form into a solvent together with maleic acid to crystallize, wherein, the molar ratio of maleic acid to the compound of formula (I) is 1:1.05-1.2;

the amount of the solvent is 8-12 times the weight of the compound of formula (I).

the reaction solvent is an alcoholic solvent and/or a mixed solvent containing an alcoholic solvent and water.

In some embodiments of the present invention, the alcoholic solvent is methanol, ethanol and/or isopropanol.

In some embodiments of the present invention, the mixed solvent of the alcoholic solvent and water is a mixed solvent of methanol, ethanol, isopropanol and water.

In some embodiments of the present invention, the volume ratio of the alcoholic solvent and water is 1:0.05-0.1.

Another purpose of the present invention is to provide the crystal type A of the compound 2 or the compound 3 for use in the manufacture of a medicament for the treatment of a disease associated with PARP receptor.

Definition and Description

Unless otherwise specified, the following terms and phrases used herein are intended to have the following meanings. A particular phrase or term should not be considered as indefinite or unclear when it is not specifically defined, but should be understood in an ordinary sense. When a trade name appears in this article, it is intended to refer to its corresponding product or its active ingredient.

The intermediate compound of the present invention can be prepared by a variety of synthetic methods well known to those skilled in the art, including the specific embodiments listed below, embodiments obtained through their combination with other chemical synthesis methods, and equivalents well known by those skilled in the art, the preferred embodiments include, but are not limited to, embodiments of the present invention.

The chemical reaction of the particular embodiments of the present invention is carried out in a suitable solvent which is suitable for the chemical changes of the present invention and the reagents and materials thereof. In order to obtain the compounds of the present invention, it is sometimes necessary for those skilled in the art to modify or select the synthetic steps or reaction schemes based on the existing embodiments.

An important consideration in any of the synthetic route schemes in the art is the selection of a suitable protecting group for a reactive functional group, such as an amino group in the present invention. Greene and Wuts (*Protective Groups In Organic Synthesis*, Wiley and Sons, 1991) are the authority of this field for the trained practitioners. All references cited herein are incorporated in their entireties.

The present invention will be specifically described below by way of Examples, which are not intended to limit the present invention in any way.

All solvents used in the present invention are commercially available and can be used without further purification. The reaction is generally carried out in an anhydrous solvent under an inert atmosphere of nitrogen gas. Proton NMR data was recorded on a Bruker Avance III 400 (400 MHz) spectrometer with chemical shifts expressed as (ppm) at low field of tetramethylsilane. Mass spectra were determined on an Agilent 1200 Series Plus 6110 (& 1956A). The LC/MS or Shimadzu MS contains one DAD: SPD-M20A (LC) and Shimadzu Micromass 2020 detector. The mass spectrometer is equipped with an electrospray ionization source (ESI) operating in positive or negative mode.

The present invention adopts the following abbreviations: DCM for dichloromethane; PE for petroleum ether; EA for ethyl acetate; DMF for N,N-dimethylformamide; DMAC for N,N-dimethylacetamide; DMSO for dimethylsulfoxide; EtOAc for ethyl acetate; tol for toluene; THF for tetrahydrofuran; EtOH for ethanol; MeOH for methanol; NMP for N-methylpyrrolidone; 2-METHF for 2-methyltetrahydrofuran; i-PrOH for 2-propanol; Bn for benzyl; Cbz for benzyloxycarbonyl, an amine protecting group; Boc for t-butylcarbonyl, an amine protecting group; Fmoc for fluorenylmethoxycarbonyl, an amine protecting group; Alloc for allyloxycarbonyl, an amine protecting group; Teoc for trimethylsilylethoxycarbonyl, an amine protecting group; $Boc_2O$ for di-tert-butyl dicarbonate; and HCl (g) for hydrogen chloride gas; $H_2SO_4$ for sulfuric acid; HOAc for acetic acid; TFA for trifluoroacetic acid; DIPEA for diisopropylethylamine; DIEA for diisopropylethylamine; NMM for N-methyl morpholine; DBU for 1,8-diazabicycloundec-7-ene; $Et_3N$ for triethylamine; LDA for bis-isopropylamine lithium; NaHMDS for sodium bis(trimethylsilyl)amide; KHMDS for potassium bis(trimethylsilyl)amide; $LiAlH_4$ for lithium aluminum hydride; t-BuOK for potassium tert-butoxide; $H_2O_2$ for hydrogen peroxide; $NH_4Cl$ for ammonium chloride; $BaSO_4$ for barium sulfate; $CaCO_3$ for calcium carbonate; $SnCl_2$ for stannous chloride; $Zn(BH_4)_2$ for zinc borohydride; $PPh_3$ for triphenylphosphine; HMDS for hexamethyldisilazane; Pd/C for palladium on carbon; $PtO_2$ for platinum dioxide; $Pd(OH)_2$ for palladium hydroxide; $Pd_2(dba)_3$ for tris(dibenzylideneacetone)dipalladium; $Pd(PPh_3)_4$ for tetrakistriphenylphosphine palladium; $Pd(dppf)_2Cl_2$ for 1,1'-bis(diphenylphosphino) ferrocenepalladium chloride; $Pd(PPh_3)_2Cl_2$ for dichlorobis(triphenylphosphine) palladium (II); $Pd(OAc)_2$ for palladium acetate; $PdCl_2$ for palladium chloride; CuI for cuprous iodide; CuBr for cuprous bromide; CuCl for cuprous chloride; Cu for copper powder; $Cu_2O$ for cuprous oxide; Xantphos for 4,5-bis(diphenylphosphino)-9,9-dimethylxanthene; Sphos for 2-dicyclohexylphosphino-2',6'-dimethoxybiphenyl; Xphos for 2-dicyclohexylphosphino-2',4',6'-triisopropylbiphenyl; Ruphos for 2-bicyclic hexylphosphino-2',6'-diisopropoxy-, 1,1'-biphenyl; Brettphos for 2-(dicyclohexylphosphino)-3,6-dimethoxy-2'-4'-6'-triisopropyl-1,1'-biphenyl; TMZ represents temozolomide.

Compounds are named manually or with ChemDraw® software, and commercial compounds use the Supplier Directory Name.

The advantages of the process for synthesizing the compound of formula (I) and the intermediate thereof provided by the present invention are as follows: the starting materials are cheap and easy to be obtained; the disadvantages of large toxicity of reagents, harsh reaction conditions, difficult separation and purification, difficult to industrialize and the like are overcome.

Specifically:

1) The raw materials of the process of the present invention for preparing the compounds of formula (I) are conventional or common reagents which are readily available in the market and inexpensive;

2) The intermediate compound (IV) cleverly utilizes two halogen groups of the intermediate compound (II) to successfully build a tricyclic structure and the amide pharmacophore through the metal catalysis and the intercalation carbonylation and amination, effectively improving the reaction yield;

3) The introduction of the isopropyl group during the preparation of the formula (I) in the present invention is achieved by reduction and hydrogenation of cheap and readily available acetone;

4) All the reagents used in each steps of the reaction are small molecules, easy to be purified.

Therefore, the present invention has high industrial application and economic value in the preparation of the compounds of formula (I) and the intermediate thereof.

X-Ray Powder Diffractometer (XRPD) Method in the Present Invention

Instrument Model: Bruker D8 advance X-ray diffractometer

Test conditions: Detailed XRPD parameters are as follows:

Light pipe: Cu, kα, (λ=1.54056 Å).
Light tube voltage: 40 kV, Light tube current: 40 mA
Divergence slit: 0.60 mm
Detector slit: 10.50 mm
Anti-scattering slit: 7.10 mm
Scanning range: 4-40 deg
Step: 0.02 deg
Step length: 0.12 seconds
Sample pan speed: 15 rpm Differential Scanning Calorimeter (DSC) Method in the Present Invention Instrument Model: TA Q2000 Differential Scanning Calorimeter Test conditions: Placing the sample (~1 mg) in the DSC aluminum pot to test at 25° C.-350° C. with a ramp rate of 10° C./min.

Thermal Gravimetric Analyzer (TGA) Method in the Present Invention

Instrument Model: TA Q5000IR Thermal Gravimetric Analyzer

Test conditions: Placing the sample (2-5 mg) in the TGA platinum pot to test at room temperature to 350° C. with a ramp rate of 10° C./min.

DETAILED DESCRIPTION OF THE PREFERRED EMBODIMENT

For a better understanding of the contents of the present invention, the following examples further illustrate the present invention, but the present invention is not limited thereto.

Example 1: Preparation of Compound 3

Scheme 1:

Step 1: Tert-butyl 4-(1-cyano-2-ethoxy-2-oxoethylidene)piperidine-1-carboxylate

A solution of tert-butyl 4-oxopiperidine-1-carboxylate (3 kg, 15.05 mol) in toluene (24 L) was heated to 95° C., and acetic acid (446 g, 7.43 mol), 2-cyanoacetate (1.68 kg, 14.85 mol), ammonium acetate (571 g, 7.41 mol) were added successively in one portion. It started to reflux to separate water when the external temperature rose to 130° C. and the internal temperature to 102° C., the complete consumption of the material was detected by HPLC when the internal temperature reached 114° C., which took about 3 hours. After the mixture was cooled to room temperature, the organic phase was washed with water (10 L), 10% aqueous $Na_2CO_3$ (8 L) and brine (5 L×2) successively. The aqueous phases were combined and extracted with ethyl acetate (5 L×2). The organic phases were combined and evaporated under reduced pressure to remove the solvent, giving 4.5 kg residue. The residue was mashed and purified with PE/EtOAc=10/1 (9 L). The white solid was collected by filtration to give the title compound (1.5 kg, yield 33.84%, purity 98.62%). (The filtrate was concentrated and further purified to give the title compound). 1H NMR (400 MHz, CHLOROFORM-d) δ ppm 1.38 (t, J=7.15 Hz, 3H), 1.50 (s, 9H), 2.79 (t, J=5.90 Hz, 2H), 3.15 (t, J=5.83 Hz, 2H), 3.56 (t, J=5.71 Hz, 2H), 3.63 (t, J=5.83 Hz, 2H), 4.31 (q, J=7.15 Hz, 2H). LCMS (ESI) m/z: 295 (M+1).

Step 2: Tert-butyl 4-(1-cyano-2-ethoxy-2-oxoethyl)-4-methylpiperidine-1-carboxylate

A 3M solution of methyl magnesium bromide (5.66 L, 16.98 mol) was added dropwise to a mixture of cuprous iodide (1.29 kg, 6.78 mol) in anhydrous tetrahydrofuran (16 L) under nitrogen atmosphere at −50 to −40° C. (with an appropriate dropping speed keeping the inter temperature below or at −40° C.). Upon the completion of the addition, the mixture was stirred at −5° C. to 0° C. for 1 hour and cooled to −50 to −40° C., and a solution of tert-butyl 4-(1-cyano-2-ethoxy-2-oxoethylidene)piperidine-1-carboxylate (2 kg, 6.79 mol) in tetrahydrofuran (4 L) was added dropwise (with an appropriate dropping speed keeping the inter temperature at or below −40° C.). After the addition, the mixture was slowly warmed to room temperature and stirred for 15 hours. The mixture was cooled to 0-5° C. and quenched with saturated aqueous ammonium chloride solution (W/W=1:1) (2 L), and then filtered with diatomaceous earth and the filtrate was separated. The residue was washed with EtOAc (5 L×2) and the combined organic layers were washed with saturated aqueous ammonium chloride (5 L×2) and brine (5 L×2) and evaporated to give the crude title compound (2.1 kg) as a yellow oil which was used directly in the next step without further purification.

Step 3: 2-(1-(tert-butoxycarbonyl)-4-methylpiperidin-4-yl)-2-cyanoacetic acid

A solution of sodium hydroxide (1.03 kg, 25.75 mol) in water (2.6 L) was added dropwise to a mixed solution of tert-butyl 4-(1-cyano-2-ethoxy-2-oxoethyl)-4-methylpiperidine-1-carboxylate (2 kg, crude, 6.44 mol) in THF/MeOH=10:1 (3.52 L) with an appropriate dropping speed keeping the inter temperature within 0-10° C. After the addition, the mixture was stirred at room temperature for 2 hours, TLC detected that the reaction was complete (the absorption of raw material & product was weak at 220 nm). A mixed solution of EtOAc (2 L)/tert-butyl methyl ether (4 L) was added and the mixture was stirred, then allowed to stand still to separate the aqueous layer. The organic phase was washed with water (1 L×3). The aqueous layers were combined and extracted with tert-butyl methyl ether (1 L×2), adjusted to pH 3-4 with 1N hydrochloric acid and extracted with DCM (5 L×2). The combined dichloromethane layers were washed with brine (5 L×2) and evaporated to give the crude title compound (1.5 kg) as a white solid, which was used directly in the next step without further purification.

Step 4: Tert-butyl 4-(cyanomethyl)-4-methylpiperidine-1-carboxylate

A mixture of 2-(1-(tert-butoxycarbonyl)-4-methylpiperidin-4-yl)-2-cyanoacetic acid (4 kg, crude, 14.17 mol) and $Cu_2O$ (405.45 g, 2.83 mol) in acetonitrile (20 mL) was stirred at 85° C. for 2 hours, TLC detected the reaction was complete (the absorption of raw material & product was weak at 220 nm). After the mixture was cooled to room temperature, the insoluble materials were filtered off and the filtrate was evaporated to dryness. The residue was dissolved with ethyl acetate (20 L), washed sequentially with 0.5N hydrochloric acid (10 L×2) and brine (20 L×2), evaporated to dryness and the residue was mashed and purified with PE/EtOAc=10/1 (16 L). The white solid was collected by filtration to give the title compound (2.5 kg, yield 74.03%, purity: being detected after equivalent amount of internal standard was added as the absorption of the product was weak at 220 nm). 1H NMR (400 MHz, CHLOROFORM-d) ppm 1.16 (s, 3H), 1.43-1.54 (m, 13H), 2.31 (s, 2H), 3.23 (ddd, J=13.68, 8.78, 4.39 Hz, 2H), 3.52-3.70 (m, 2H). LCMS (ESI) m/z: 239 (M+1).

Step 5: Tert-butyl 4-(1-cyano-2-oxoethyl)-4-methyl-piperidine-1-carboxylate

2M LDA (3.15 L, 6.3 mol) was added dropwise to a mixture of tert-butyl 4-(cyanomethyl)-4-methylpiperidine-1-carboxylate (1 kg, 4.2 mol) in THF (8 L) under nitrogen atmosphere at −60 to −50° C. After being stirred at −60 to −50° C. for 1 hour, the reaction solution was added with ethyl formate (622 g, 8.4 mol) dropwise. After the addition, the reaction solution was slowly heated to room temperature and stirred for 15 hours. After the reaction was complete, the reaction solution was cooled to −30 to −20° C., quenched with 1N aqueous hydrochloric acid (5 L) and the aqueous layer was extracted with EtOAc (2 L×3). The combined organic layers were washed with 0.5N hydrochloric acid (5 L×2) and brine (5 L×2), evaporated to dryness and the residue was purified by being mashed with PE/EtOAc=10/1 (2 L). The white solid was collected by filtration to give the title compound (900 g, yield 80.46%, purity 100%). 1H NMR (400 MHz, CHLOROFORM-d) ppm 1.22 (s, 3H), 1.47-1.55 (m, 11H), 1.73-2.07 (m, 4H), 3.38-3.48 (m, 4H), 6.97 (s, 1H), 7.55-8.14 (m, 1H). LCMS (ESI) m/z: 289 (M+23).

Step 6: (2,6-dibromo-4-fluorophenyl)hydrazine hydrochloride

A solution of sodium nitrite (141 g, 2.05 mol) in water (1.8 L) solution was slowly added dropwise to a solution of 2,6-dibromo-4-fluoroaniline (500 g, 1.86 mol) in concentrated hydrochloric acid (1.8 L) at −5 to 0° C. After the addition, the reaction mixture was stirred at −5 to 0° C. for 40 minutes, and the mixture was added to a solution of stannous chloride dihydrate (629 g, 2.79 mol) in concentrated hydrochloric acid (2 L) dropwise at −10 to −5° C. with an appropriate dropping speed that kept the inter temperature at or below −5° C. The resultant mixture was slowly heated to about 20° C. and stirred for 12 hours. The solid was collected by filtration, washed with isopropanol (0.5 L×4) and dried in vacuo to give the title compound (430 g, yield 72%, purity 97.75%) as an off-white solid which can be used in the next step without further purification. 1H NMR (400 MHz, DMSO-d6) δ ppm 2.37-2.68 (m, 1H), 6.94-7.28 (m, 1H), 7.80 (d, J=8.03 Hz, 2H), 10.13 (br. s., 3H).

Step 7: Tert-butyl 4-(5-amino-1-(2,6-dibromo-4-fluorophenyl)-1H-pyrazol-4-yl)-4-methylpiperidine-1-carboxylate A mixture of potassium acetate (1.11 kg, 11.27 mol) and (2,6-dibromo-4-fluorophenyl)hydrazine hydrochloride (2.65 kg, 8.27 mol) in ethanol (25 L) was stirred at room temperature for 0.5 hours, then tert-butyl 4-(1-cyano-2-oxoethyl)-4-methylpiperidine-1-carboxylate (2 kg, 7.51 mol) was added and the mixture was stirred at 60° C. for 2 hours. After completion of the reaction, NaHCO3 (1.89 kg, 22.5 mol) was added portionwise to the mixture and stirred for another 15 hours at 80 to 90° C. After being cooled to room temperature, the resulting mixture was evaporated and the residue was quenched with water (20 L) and extracted with EtOAc (10 L×2). The combined organic layer was washed with brine (10 L×2), evaporated and the residue was mashed and purified with PE/EtOAc=10/1 (6 L). The white solid was collected by filtration to give the title compound (3.5 kg, yield 87.5%, purity 99.84%). 1H NMR (400 MHz, CHLOROFORM-d) ppm 1.32 (s, 3H), 1.48 (s, 9H), 1.57-1.63 (m, 2H), 2.03-2.14 (m, 2H), 3.30 (br. s., 4H), 3.67 (d, J=13.30 Hz, 2H), 7.41-7.52 (m, 3H).

Scheme 2:

Compound 1

Compound 3

Step 1: Tert-butyl 4-(8-bromo-6-fluoro-4H-benzo[4,5]imidazo[1,2]pyrazol-3-yl)-4-methylpiperidine-1-carboxylate

A mixture of tert-butyl 4-(5-amino-1-(2,6-dibromo-4-fluorophenyl)-1H-pyrazol-4-yl)-4-methylpiperidine-1-carboxylate (2.1 kg, 3.95 mol), Pd₂(dba)₃ (289.37, 0.316 mol), Xantphos (365.69, 0.632 mol) and cesium carbonate (2.57 kg, 7.9 mol) in DMF (16.8 L) was stirred at 125 to 135° C. for 5-6 hours under nitrogen atmosphere. After being cooled to room temperature, the resulting mixture was filtered through celite. The filtrate was diluted with EtOAc (20 L) and water (40 L) and stirred to portion. The aqueous phase was extracted with ethyl acetate (20 L×2) and the organic phase was evaporated under reduced pressure to dryness to give the crude title compound (2.68 kg) which was used in the next step without further purification. LCMS (ESI) m/z: 451, 453 (M, M+2).

Step 2: Tert-butyl 4-(8-carbamoyl-6-fluoro-4H-benzo[4,5]imidazo[1,2-B]pyrazol-3-yl)-4-methylpiperidine-1-carboxylate A 10 L autoclave was charged with tert-butyl 4-(8-bromo-6-fluoro-4H-benzo[4,5]imidazo[1,2-B]pyrazol-3-yl)-4-methylpiperidine-1-carboxylate (535 g, 1.19 mol), HMDS (956.55 g, 5.93 mol), Pd(dppf)Cl₂ (43.37 g, 0.0593 mol), Xantphos (34.29 g, 0.0593 mol), DIPEA (306.40 g, 2.37 mol) and DMF (5 L), and purged with carbon monoxide for 3 times, pressurized to 0.8 to 1 MPa, heated to 100 to 110° C. and stirred for 18-20 hours. After being cooled to room temperature, the mixture was filtered through celite. The filtrate was diluted with ethyl acetate (5 L) and water (15 L) and stirred to portion. The aqueous phase was extracted with ethyl acetate (5 L×2), and the organic phase was washed with brine (5 L) and concentrated to dryness under reduced pressure to give the crude title compound (552 g, crude) which was used in the next step without further purification. LCMS (ESI) m/z: 416 (M+1).

Step 3: 6-fluoro-3-(4-methylpiperidin-4-yl)-4H-benzo[4,5]imidazo[1,2-b]pyrazol-8-carboxamide A 4M HCl(g)/MeOH solution was added dropwise to a solution of tert-butyl 4-(8-carbamoyl-6-fluoro-4H-benzo[4,5]imidazo[1,2-B]pyrazol-3-yl)-4-methylpiperidine-1-carboxylate (2.7 kg, 6.5 mol) in MeOH (10 L) at −10 to 0° C. After the addition, the reaction solution was heated to 20-25° C. and stirred for 2-3 hours. After the reaction was completed, the resulting mixture was concentrated to 5 L and filtered to obtain solid. The solid was dispersed in water (12 L), and the mixture was cooled to 0 to 5° C., and 20% sodium hydroxide solution (1 L) was added dropwise slowly to pH 9-10, after the addition, the mixture was stirred at 0 to 5° C. for 1 hour, filtered and the filter cake was washed with water until it was neutral and dried to give the title compound (1.03 kg, yield 82%, purity 99.72%) as a pale yellow solid. 1H NMR (400 MHz, DMSO-d6) ppm 1.31 (s, 3H), 1.68-1.85 (m, 2H), 2.27 (d, J=14.81 Hz, 2H), 2.83 (t, J=9.79 Hz, 2H), 3.00-3.13 (m, 2H), 7.42 (dd, J=8.66, 2.51 Hz, 1H), 7.53 (dd, J=11.11, 2.57 Hz, 1H), 7.78 (s, 1H), 8.06 (s, 1H), 10.66 (s, 1H). LCMS (ESI) m/z: 316 (M+1).

Step 4: 6-fluoro-3-(1-isopropyl-4-methylpiperidin-4-yl)-4H-benzo[4,5]imidazo[1,2-b]pyrazol-8-carboxamide

Compound¹

A 10 L autoclave was charged with 6-fluoro-3-(4-methylpiperidin-4-yl)-4H-benzo[4,5]imidazo[1,2-b]pyrazol-8-formamide (505 g, 1.6 mol), 10% Pd/C (51 g), acetone (930.12 g, 16 mol) and NMP (5 L), and purged with hydrogen gas for 3 times, pressurized to 0.8 to 1 MPa, heated to 60 to 70° C. and stirred for 18-20 hours. After being cooled to room temperature, the mixture was filtered through celite. The filtrate was poured into water (20 L) and filtered with stirring. The filter cake was washed with water until it was neutral and dried to give the title compound as a pale yellow solid (405 g, yield 78.8%, purity 99.05%). 1H NMR (400 MHz, DMSO-d6) ppm 0.92 (d, J=6.53 Hz, 6H), 1.26 (s, 3H), 1.58-1.75 (m, 2H), 1.86-1.93 (m, 1H), 2.09-2.20 (m, 2H), 2.35 (t, J=7.72 Hz, 2H), 2.63-2.74 (m, 2H), 7.43 (dd, J=8.41, 2.64 Hz, 1H), 7.59 (dd, J=11.11, 2.57 Hz, 1H), 7.76 (s, 1H), 8.12 (s, 1H), 10.62 (s, 1H). LCMS (ESI) m/z: 358 (M+1).

Step 5: 6-fluoro-3-(1-isopropyl-4-methylpiperidin-4-yl)-4H-benzo[4,5]imidazo[1,2-b]pyrazol-8-formamide.maleate monohydrate Compound³

A solution of 6-fluoro-3-(1-isopropyl-4-methylpiperidin-4-yl)-4H-benzo[4,5]imidazo[1,2-b]pyrazol-8-formamide (0.404 kg, 1.13 mol) and maleic acid (0.137 kg, 1.18 mol) in 95% methanol (5.25 L) was heated to reflux for 2 hours and then filtered when hot. The filtrate was allowed to stand to portion and cool, then filtered to give a white crystal (420 g, yield 78.2%, purity 99.66%). 1H NMR (400 MHz, DMSO-d6) ppm 0.63-1.70 (m, 10H), 1.81-2.32 (m, 3H), 2.82 (br. s., 1H), 3.11-3.36 (m, 4H), 6.04 (s, 2H), 7.52 (dd, J=8.28, 2.51 Hz, 1H), 7.62 (dd, J=11.04, 2.51 Hz, 1H), 7.77-7.98 (m, 1H), 8.16 (s, 1H), 8.91 (br. s., 1H), 10.54 (br. s., 1H), 12.20 (br. s., 1H). LCMS (ESI) m/z: 358 (M+1).

Stability Test for Crystal Type A in Different Solvents

A certain number of aliquots of 50 mg of Crystal type A were weighed out, and added with 0.3 to 0.4 mL single or mixed solvent as listed below respectively, and the mixture was stirred at 25° C. After being stirred for 3 days, the samples were centrifuged and the solid in all samples were collected. XRPD was used to determine the crystalline state. The results were shown in Table 2.

TABLE 2

Stability test of Crystal type A in different solvents

| No. | Solvent | Appearance (3 days) | Results |
|---|---|---|---|
| 1 | Methanol | Suspension | Crystal type A |
| 2 | Ethanol | Suspension | Crystal type A |
| 3 | Isopropanol | Suspension | Crystal type A |
| 4 | Acetone | Suspension | Crystal type A |
| 5 | Ethyl acetate | Suspension | Crystal type A |
| 6 | Methanol:water = 3:1 | Suspension | Crystal type A |
| 7 | Ethanol:water = 3:1 | Suspension | Crystal type A |
| 8 | Acetonitrile:water = 1:1 | Suspension | Crystal type A |
| 9 | Acetone:water = 1:2 | Suspension | Crystal type A |
| 10 | Isopropanol:water = 1:1 | Suspension | Crystal type A |

Solid Stability Test for Crystal Type a Under the Conditions of High Temperature, High Humidity and Strong Illumination A sample of Crystal type A (about 10 mg) was weighed out, placed at the bottom of a glass vial and spread into a thin layer. The sample placed at 60° C. and 92.5% relative humidity was sealed with aluminum foil at the vial mouth, and the aluminum foil was pricked to ensure that the sample was fully exposed to the ambient air; the sample placed under strong illumination (5 Klux) was sealed with a screw cap. The samples placed under different conditions were sampled and tested on the 10th day. The test results were compared with the initial test results on the 0th day. The test results are shown in the following Table 3:

TABLE 3

Solid stability test for Crystal type A

| Test conditions | Sampling time (Day) | Appearance | Content (%) | Total impurities (%) |
|---|---|---|---|---|
| — | 0 | White powder | 98.9 | 0.10 |
| 60° C. (open) | 10 | White powder | 98.5 | 0.11 |
| 92.5% RH (open) | 10 | White powder | 99.5 | 0.10 |

TABLE 3-continued

Solid stability test for Crystal type A

| Test conditions | Sampling time (Day) | Appearance | Content (%) | Total impurities (%) |
|---|---|---|---|---|
| Strong illumination (sealed) | 10 | White powder | 99.4 | 0.11 |

Evaluation of In Vitro Activity

Cell PARylation Analysis

HCC1937 cells were seeded into a 965-well plate at 4×104 cells/well and cultured in a 37° C. incubator overnight. After the cells were treated with the test compound for 30 minutes, they were treated with 1 mM hydrogen peroxide for 10 minutes. Cells were washed twice with 200 UL of precooled PBS and fixed with 100 ul of precooled methanol/acetone (7:3) for 30 minutes in an ice bath. After being air-dried, they were blocked with PBS-Tween-20 blocking solution (0.05%) with 5% nonfat dry milk dissolved at room temperature for 30 minutes. Cells and anti-PAR 10H antibody in a ratio of 1:100 were incubated in a blocking solution at room temperature for 1 hour and then washed with PBS-Tween-20 for three times, and added into a blocking solution containing goat anti-mouse fluorescein-5 (6) thiocyanate (FITC)-based secondary antibody and 1 μg/mL DAPI to be incubated at room temperature in the dark for 1 hour. After being washed with PBS-Tween-20 for three times, the data was analyzed using a fluorescent microplate counter (Flexstation III, Molecular Device). PARP enzyme assay (according to the instruction of HT universal PARP1 colorimetric assay kit). Histones were packaged in a 96-well plate and incubated overnight at 4° C. After being washed with 200 UL PBST solution for three times, the plate was blocked with blocking solution, incubated for 30 minutes at room temperature and washed with PBST solution for three times. The compounds to be tested were added to the well plate and then 20 ml of diluted PARP1 (1 nM) or 20 ml of PARP2 (3 nM) was added to the reaction system and incubated for 1 or 2 hours. A mixed of streptavidin-HRP (1:50) (50 μl) was added to the well plate and incubated at room temperature for 30 minutes, and washed with the PBST buffer for three times. 100 ml (HRP) (Chemiluminescent Substrate A and Substrate B (1:1)) was added to the well plate. Read immediately onto a microplate reader (Envision, PerkinElmer).

Anti-Proliferation Test

MDA-MB-436 and MDA-MB-231 cells were seeded in a 96-well plate at a density of 500 and 2000 cell per well, respectively, and cultured overnight. The medium was RPMI 1640 containing 10% (v/v) FBS and 1% (v/v) penicillin-streptomycin. They were treated for 8 days after the compound to be tested was added. Cell viability was measured by CCK8 kit. Specifically, 10 UL CCK8 reagent was added to each well and incubated in a 5% CO2 incubator at 37° C. for 3 hours. After shaking for 10 minutes, the light absorbance (OD value) was measured with a Flexstation III (Molecular Device) at 450 nm.

For the test of compound combinations (in combination with DNA damage drugs), the PF50 value was used to calculate the synergistic effect of the drug. PF50=[IC50 of the tested compound]/[IC50 of the compound at a fixed DNA damage drug concentration]. Temozolomide (TMZ) was used as DNA damage drug in this study.

IC50 data of inhibition of MDA-MB-231/436 cell proliferation by Compound 1 and ABT888 when used singly and synergistically with TMZ are shown in Table 4 below:

TABLE 4

In vitro screening test results of the compounds of the present invention

| | MDA-MB-231 | | | | | MDA-MB-436 | | | |
|---|---|---|---|---|---|---|---|---|---|
| Compound No. | IC50_N = 1 (uM) | IC50_N = 2 (uM) | IC50_Avg (uM) | PF50 | Compound No. | IC50_N = 1 (uM) | IC50_N = 2 (uM) | IC50_Avg (uM) | PF50 |
| ABT-888 | 44.04 | 36.99 | 40.51 | | ABT-888 | 0.444 | 0.167 | 0.305 | |
| ABT-888 combined with 1 uM TMZ | 25.46 | 35.96 | 30.71 | 1.32 | ABT-888 combined with 25 uM TMZ | 0.026 | 0.010 | 0.018 | 17.14 |
| TMZ | 4.61 | 3.72 | 4.17 | | TMZ | 80.18 | 141.93 | 111.06 | |
| Compound 1 | 6.21 | 5.44 | 5.83 | | Compound 1 | 0.089 | 0.053 | 0.071 | |
| Compound 1 combined with 1 uM TMZ | 3.96 | 5.75 | 4.86 | 1.20 | Compound 1 combined with 25 uM TMZ | 0.009 | 0.005 | 0.007 | 9.84 |
| TMZ | 3.33 | 3.52 | 3.42 | | TMZ | 152.3 | 61.66 | 106.98 | |

Conclusion: Compound 1 shows a strong inhibitory effect on BRAC mutant MDA-MB-436 cell line and shows good synergistic effect combined with TMZ.

What is claimed is:

1. A process for preparing a compound represented by formula (IV), comprising:

-continued (IV)

wherein, the ammonia source is HMDS and/or formamide;

$R_1$ is an amino protecting group;

X is a halogen;

the metal catalyst is a palladium metal catalyst and/or a copper metal catalyst;

the ligand is a phosphine-containing ligand coordinated to a palladium metal catalyst and/or a nitrogen-containing ligand coordinated to a copper metal catalyst; and the base is an alkali metal base, an alkaline earth metal base, an organic base and/or an organometallic base.

2. A process for preparing a compound represented by formula (I), comprising:

(III)

wherein, the ammonia source is HMDS and/or formamide;

$R_1$ is an amino protecting group;

X is a halogen;

the metal catalyst is a palladium metal catalyst and/or a copper metal catalyst;

the ligand is a phosphine-containing ligand coordinated to a palladium metal catalyst and/or a nitrogen-containing ligand coordinated to a copper metal catalyst;

the base is an alkali metal base, an alkaline earth metal base, an organic base and/or an organometallic base;

HB is an organic or inorganic acid;

HA is an organic or inorganic acid;

R is selected from the group consisting of methyl, ethyl, isopropyl or tert-butyl; and the hydrogen source is hydrogen gas.

3. The process according to claim 2, wherein the organic acid is selected from the group consisting of trifluoroacetic acid, methanesulfonic acid, p-toluenesulfonic acid, citric acid, maleic acid or fumaric acid; or the inorganic acid is selected from the group consisting of hydrochloric acid, hydrobromic acid, phosphoric acid and/or sulfuric acid.

4. The process according to claim 1, wherein $R_1$ is an alkoxycarbonyl amino protecting group or a benzyl amino protecting group;

the palladium metal catalyst is selected from the group consisting of $Pd_2(dba)_3$, $Pd(PPh_3)_4$, $Pd(dppf)Cl_2$, $Pd(PPh_3)_2Cl_2$, $Pd(OAc)_2$ and/or $PdCl_2$;

the copper metal catalyst is selected from the group consisting of CuI, CuBr, CuCl, Cu and/or Cu$_2$O;

the phosphine-containing ligand coordinated to the palladium metal catalyst is Xantphos, Sphos, Xphos, Ruphos and/or Brettphos;

the nitrogen-containing ligand coordinated to the copper metal catalyst is 1,2-cyclohexanediamine, N,N'-dimethylethylenediamine and/or 1,10-phenanthroline;

the alkali metal base is selected from the group consisting of lithium hydroxide, sodium hydroxide, potassium hydroxide, cesium hydroxide, sodium carbonate, potassium carbonate, cesium carbonate, sodium bicarbonate, potassium bicarbonate and/or potassium phosphate;

the alkaline earth metal base is sodium hydride, potassium hydride and/or calcium hydride;

the organic base is triethylamine, DIPEA, NMM and/or DBU; and the organometallic base is sodium methoxide, lithium tert-butoxide, sodium tert-butoxide, potassium tert-butoxide, sodium ethoxide and/or aluminum isopropoxide.

5. Crystal type A of compound 3, characterized by an XRPD pattern as shown in FIG. 1, Compound 3

6. The crystal type A according to claim 5, characterized by a differential scanning calorimetry curve with a starting point of the endothermic peak at 85.44° C., 162.95° C., and 205.63° C.±3° C. respectively.

7. The crystal type A according to claim 5, characterized by a DSC Spectrogram Data as shown in FIG. 2.

8. The crystal type A according to claim 5, characterized by a thermogravimetric profile with weight loss of up to 3.740% at 129.34° C., up to 0.4250% at 194.30° C. and up to 13.59% at 245.46° C.

9. The crystal type A according to claim 5, characterized by a TGA Spectrogram Data as shown in FIG. 3.

10. A process for preparing the crystal type A according to claim 5, comprising adding the compound of formula (I) in any form into a solvent together with maleic acid to crystallize, wherein,

IIA the molar ratio of maleic acid to the compound of formula (I) is 1:1.05-1.2;

the amount of the solvent is 8-12 times the weight of the compound of formula (I); and the solvent is an alcoholic solvent and/or a mixed solvent containing an alcoholic solvent and water;

wherein, the alcoholic solvent is methanol, ethanol and/or isopropanol;

wherein, the mixed solvent of the alcoholic solvent and water is a mixed solvent of methanol, ethanol, isopropanol and water; and wherein, the volume ratio of the alcoholic solvent and water is 1:0.05-0.1.

11. A method for inhibiting PARP activity in a subject, comprising: administering an effective amount of a salt according to claim 6 to the subject.

12. A method for inhibiting PARP activity in a subject, comprising: administering an effective amount of crystal type A according to claim 5 to the subject.

13. The process according to claim 2, wherein R$_1$ is an alkoxycarbonyl amino protecting group or a benzyl amino protecting group;

the palladium metal catalyst is selected from the group consisting of Pd$_2$(dba)$_3$, Pd(PPh$_3$)$_4$, Pd(dppf)Cl$_2$, Pd(PPh$_3$)$_2$Cl$_2$, Pd(OAc)$_2$ and/or PdCl$_2$;

the copper metal catalyst is selected from the group consisting of CuI, CuBr, CuCl, Cu and/or Cu$_2$O;

the phosphine-containing ligand coordinated to the palladium metal catalyst is Xantphos, Sphos, Xphos, Ruphos and/or Brettphos;

the nitrogen-containing ligand coordinated to the copper metal catalyst is 1,2-cyclohexanediamine, N,N'-dimethylethylenediamine and/or 1,10-phenanthroline;

the alkali metal base is selected from the group consisting of lithium hydroxide, sodium hydroxide, potassium hydroxide, cesium hydroxide, sodium carbonate, potassium carbonate, cesium carbonate, sodium bicarbonate, potassium bicarbonate and/or potassium phosphate;

the alkaline earth metal base is sodium hydride, potassium hydride and/or calcium hydride;

the organic base is triethylamine, DIPEA, NMM and/or DBU; and the organometallic base is sodium methoxide, lithium tert-butoxide, sodium tert-butoxide, potassium tert-butoxide, sodium ethoxide and/or aluminum isopropoxide.

* * * * *